United States Patent [19]

Stropkay et al.

[11] Patent Number: 5,919,156

[45] Date of Patent: *Jul. 6, 1999

[54] IONTOPHORETIC DRUG DELIVERY SYSTEM, INCLUDING UNIT FOR DISPENSING PATCHES

[75] Inventors: Scott Edward Stropkay, Carlisle, Mass.; Michael I. Bernhard, Summit, N.J.

[73] Assignee: Becton, Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/722,760

[22] Filed: Sep. 27, 1996

[51] Int. Cl.[6] .................................................. A61N 1/30
[52] U.S. Cl. ............................... 604/20; 424/449
[58] Field of Search ............................... 604/20; 424/449

[56] References Cited

U.S. PATENT DOCUMENTS

| | | | |
|---|---|---|---|
| 4,942,883 | 7/1990 | Newman | 128/798 |
| 5,498,235 | 3/1996 | Flower | 604/20 |
| 5,562,607 | 10/1996 | Gyory | 604/20 |
| 5,603,693 | 2/1997 | Frenkel | 604/20 |

*Primary Examiner*—D. Gabrielle Brouillette
*Attorney, Agent, or Firm*—Royal N. Ronning, Jr.; Allen W. Wark

[57] ABSTRACT

An iontophoretic drug delivery system including a plurality of patches, at least one reusable controller and a unit for storing and dispensing the patches. The patches may be secured in a compartment formed in the unit and the controller may be stored in another compartment formed in the unit. In this way, the reusable controller and a new patch can be removed from the unit and fastened to one another for activation and attachment to the skin of a patient.

1 Claim, 2 Drawing Sheets

IONTOPHORETIC DRUG DELIVERY SYSTEM, INCLUDING UNIT FOR DISPENSING PATCHES

FIELD OF THE INVENTION

The present invention generally relates to iontophoretic drug delivery systems, and more specifically relates to a unit for dispensing new patches and/or for collecting used patches.

BACKGROUND OF THE INVENTION

Transdermal drug delivery systems have, in recent years, become an increasingly important means of administering drugs and like therapeutic agents.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament." Such systems offer advantages clearly not achievable by any other methods of administration, such as avoiding introduction of the drug through the gastrointestinal tract or punctures in the skin to name a few.

Conventional iontophoretic devices, such as those described in U.S. Pat. No. 4,820,263 (Spevak et al.), U.S. Pat. No. 4,927,408 (Haak et al.) and U.S. Pat. No. 5,084,008 (Phipps), the disclosures of which are hereby incorporated by reference, for delivering a drug or medicine transdermally through iontophoresis, basically consist of two electrodes, which are in contact with a portion of a patient's body. A first electrode, generally called the active electrode, delivers the ionic substance or drug into the body by iontophoresis. The second electrode, generally called the counter electrode, closes an electrical circuit that includes the first electrode and the patient's body. Generally, the circuit includes a source of electrical energy, such as a battery. The ionic substance to be driven into the body may be either positively charged or negatively charged. In the case of a positively charged ionic substance, the anode of the iontophoretic device becomes the active electrode and the cathode serves as the counter electrode to complete the circuit. Alternatively, if the ionic substance to be iontophoretically delivered is negatively charged, the cathode will be the active electrode and the anode will be the counter electrode.

In practice, this process is typically achieved by placing the ionic drug either in solution or in gel form on a carrier and placing the drug-containing carrier, for example, in the form of a drug-filled adhesive patch, into contact with the skin. The pair of electrodes is placed in contact with the skin and with the carrier. Direct current is applied between the two electrodes. Under the influence of the electric field present, the drug molecules migrate through the skin. As current flows between the two electrodes placed at spaced apart locations on the skin, the current path carries the drug with it.

However, problems and limitations have been associated with prior devices, particularly with respect to storing and/or dispensing patches for use with reusable controllers and the like. In addition, there has been a problem associated with disposal of used patches, which may contain some unused quantity of the drug.

Thus, there has been a need for an iontophoretic drug delivery system, including a unit for dispensing and/or collecting patches, which would eliminate the problems and limitations associated with the prior devices discussed above, most significant of the problems being associated with dispensing patches for use with reusable controllers and for collecting used patches.

SUMMARY OF THE INVENTION

In contrast to the prior devices and systems discussed above, it has been found that a iontophoretic drug delivery system may be constructed in accordance with the present invention which can be easily used to dispense new patches and/or collect used patches. Users of such a system may include the patient as well as doctors, nurses and the like.

The iontophoretic drug delivery system of the present invention for use in delivering at least one medication through an applied area of a patient, such as the skin, mucus membrane and the like, including at least one controller and a plurality of patches for attachment one at a time to the skin of a patient, with each patch containing an active compound to be delivered, and unit means for storing the patches therein and for storing the controller therein so that a patch may be dispensed from the unit means and fastened to the controller for attachment to the skin of the patient to iontophoretically delivery the active compound contained in the patch to the patient.

In the preferred embodiment of the iontophoretic drug delivery system, the unit means includes a housing having a bottom end, a top end and at least one compartment therein, with the patches being stored in the compartment and dispensed therefrom through the bottom end. Also, the bottom end includes a slot through which the patches are dispensed and the top end includes a slot through which used patches may be inserted for collection in the compartment. The iontophoretic drug delivery system also includes a second compartment for storing the controller therein and charging means associated with the second compartment for charging the controller between uses.

The unit of the present invention for storing and dispensing patches for use in iontophoretically delivering at least one medication through an applied area of a patient, such as the skin, mucus membrane and the like, includes a housing having a top end, a bottom end at least one central compartment for storing a plurality of patches therein, the bottom end including a slot through which the patches may be dispensed, the top including a slot through which used patches may be inserted for collection in the housing, and a storage compartment for storing at least one controller for use with the patches.

The preferred embodiment of the iontophoretic drug delivery system also includes charging means associated with the storage compartment for charging the controller between uses, and means for providing an audible signal to indicate when a patch is to be replaced.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

DETAILED DESCRIPTION OF THE PREFERRED EMBODIMENT

Figure 1:
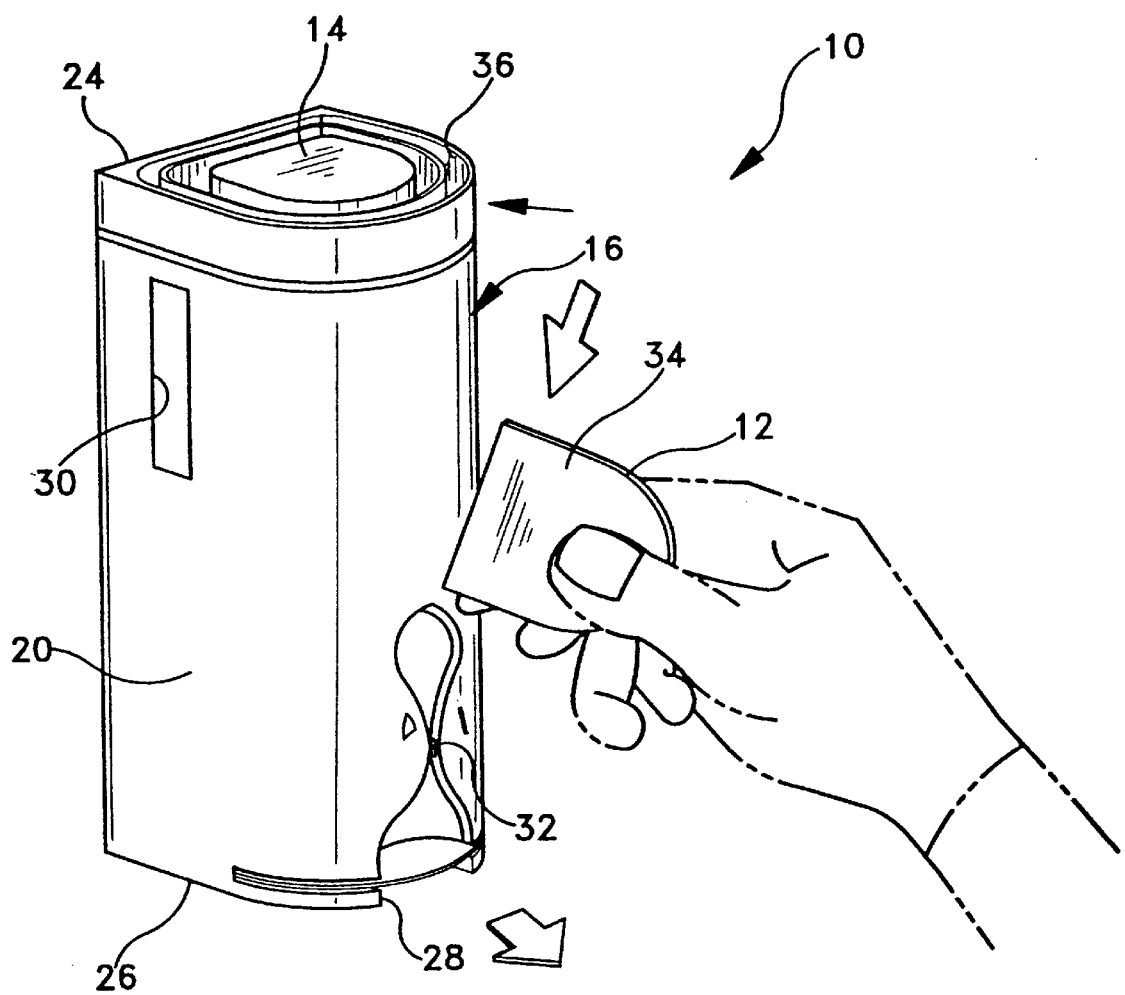
FIG. 1 is a perspective view of the iontophoretic drug delivery system of the present invention, including the unit for dispensing new patches and/or collecting used patches.
Figure 2:
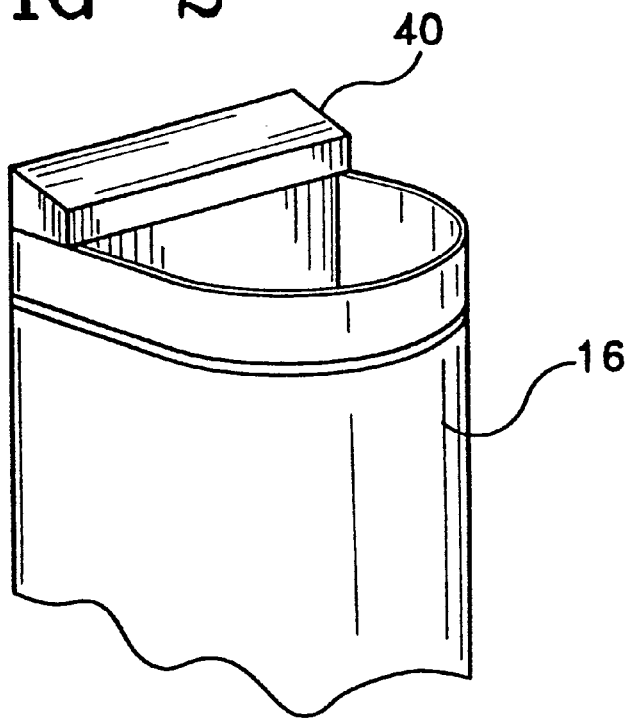
FIG. 2 is an fragmentary perspective view of the iontophoretic drug delivery system, particularly the portion of the unit for storing the controller.
Figure 3:
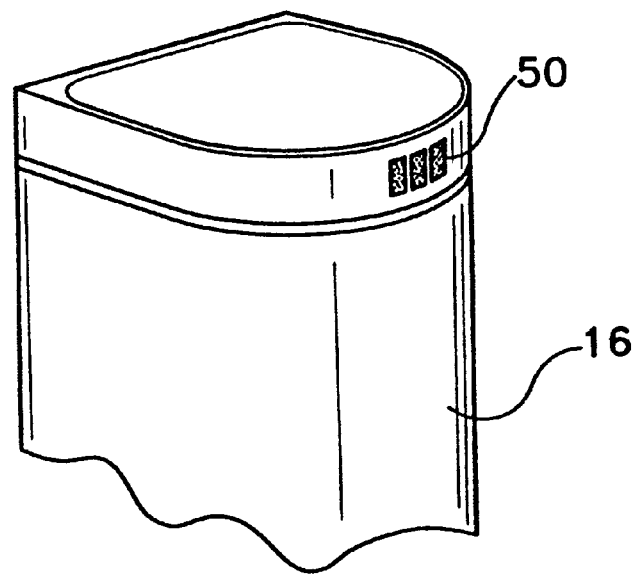
FIG. 3 is an fragmentary perspective view of an alternative embodiment of the iontophoretic drug delivery system, particularly the top end of the unit which includes means for indicating that a patch needs to be replaced.

The iontophoretic drug delivery system or kit of the present invention is illustrated in FIGS. 1–3 and generally includes the designation 10. Referring to FIGS. 1 and 2, the system 10 of the present invention includes at least one patch 12, a controller 14 and a unit 16.

The particular patch 12 is not essential to the present invention and typically includes an electrode assembly, having at least two electrodes and corresponding electrode reservoirs as disclosed in co-pending application (Attorney docket number P-3764), entitled "IONTOPHORETIC DRUG DELIVERY SYSTEM, INCLUDING METHOD FOR ACTIVATING SAME FOR ATTACHMENT TO PATIENT," the disclosure of which is hereby incorporated by reference in its entirety. Also, the drug may be contained in a separate reservoir or in one of the electrode reservoirs. The patch is preferably held together by a suitable supporting structure. The medication or drug is preferably in an ionized or ionizable form.

Referring to FIG. 1, the unit 16 includes a housing 20 having at least one internal compartment 22 for storing patches 12. In the preferred embodiment, the housing is a generally tubular shaped cylinder having a top end 24 and a bottom end 26. The patches are stacked or likewise arranged in the compartment 22 of the housing and dispensed or otherwise removed therefrom through a slot 28 provided along the bottom end 26. Also, a slot 30 may be provided at the top end through which used patches may be inserted. In this way, the unit 16 can be used to dispense new patches as well as collect used patches therein for subsequent disposal. It should be appreciated that other shapes and configurations may be used, for example, a generally square shape or palm conforming shape may be utilized.

Also, an opening means may be included on the housing in the form, for example, of a slitter 32 for opening each individual package 34 containing a patch. The particular means for opening is not essential to the present invention and will depend upon the particular package used, which may include a laminated package as disclosed in application Ser. No. 08/316,741, entitled "METHOD FOR FORMING AND PACKAGING IONTOPHORETIC DRUG DELIVERY PATCHES AND THE LIKE TO INCREASE STABILITY AND SHELF-LIFE," the disclosure of which is hereby incorporated by reference in its entirety.

In addition, a storage compartment 36 may be provided at the top of the housing in which the controller 14 may be stored between uses. In this way, the system may include the controller and at least a portion of the patches necessary for delivery of the drug during a prescribed regiment, which for example, may be ten days or thirty days, depending upon the drug to be delivered. Accordingly, the controller 14 is preferably reusable and releasably attachable to the patch 12. The particular controller is not essential to the present invention, but must include the microprocessor for controlling the supply of current delivered by the power source, and may include, for example, those disclosed in co-pending patent application Ser. No. 08/315,532, entitled "IONTO-PHORESIS PATCH/CONTROLLER INTERCONNECTION USING A CONDUCTIVE ELASTOMER TO PROVIDE NOISE-FREE ELECTRICAL CONTACT BETWEEN PATCH AND CONTROLLER," Ser. No. 08/315,533 entitled "IONTOPHORESIS ASSEMBLY INCLUDING CLEANABLE ELECTRICAL CONTACTS," Ser. No. 08/315,372 entitled "APPARATUS AND METHOD FOR ENSURING COMPATIBILITY OF A REUSABLE IONTOPHORETIC CONTROLLER WITH AN IONTOPHORETIC PATCH," and Ser. No. 08/534,897 entitled "IONTOPHORETIC DRUG DELIVERY SYSTEM, INCLUDING REUSABLE DEVICE," and U.S. Pat. No. 5,498,235 (Flower), the disclosures of which are hereby incorporated by reference in their entirety.

In addition, because of limited battery life, it may be ecessary for the controller 14 to be rechargeable. Accordingly, as illustrated in FIG. 2, the unit 16 may include a recharger 40 so that the controller may be placed in the compartment 34 and recharged between uses. Also, in the event that the controller 14 is to be used to deliver the drug over a twenty-four hour period, it may be necessary to provide an additional controller with the unit so that one can be worn while the other in being recharged. Therefore, it may be desirable for the housing to include means, which would not permit the controller 14 to be removed until fully recharged. In this way, the user would be unable to remove the controller from the housing for fastening to a patch 12, unless sufficient charge is available to delivery the drug over the desired period of time.

Also, in yet another embodiment illustrated in FIG. 3, a means such as a buzzer 50 is provided in the top of the housing for providing an audible signal to indicate when a patch is to be replaced.

Operation and Use

Having described the preferred embodiment of the iontophoretic drug delivery system 10, including the disposable patches 12, reusable controller 14 and unit 16, of the present invention, its operation and use is described below in connection with FIG. 1.

As illustrated in FIG. 1, a patch 12 contained in a package is removed from the unit 16 through the slot 28 and the package 34 is opened. Next, the patch is releasably fastened to the controller 14 for activation and attachment to the skin of the patient.

As is well known within the field, the device can be attached to a suitable area of the skin of the patient, with the drug containing patch in electrical conducting contact with the skin, and a voltage impressed across the electrodes of the electrode assembly to cause current to flow through the skin of the patient to drive the drug into the skin and the tissue to be absorbed by the body of the patient for the desired period of time. It should also be appreciated that the device of the present invention can be applied to other areas of the body such as mucus membranes depending upon the desired therapy and drugs to be delivered.

Active agent, drug, formulation, medication, medicament and active compound have been used herein to mean at least one pharmaceutical agent, such as therapeutic compounds, diagnostic agents, anesthetic agents and the like.

While the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

In addition, while the preferred embodiments of the present invention has been described so as to enable one skilled in the art to practice the system and method of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A unit for storing and dispensing patches for use in iontophoretically delivering at least one active compound through an applied area of a patient, said area including skin or mucus membrane, comprising:

a housing having a top end, a bottom end and at least one central compartment for storing a plurality of patches, wherein said plurality of patches contains at least one active compound for delivery to a patient, with the patches being arranged in said central compartment;

said bottom end including a slot through which unused patches may be removed from said central compartment for fastening to a controller and for attachment to the skin of the patient to permit iontophoretic delivery of the active compound contained in the unused patches to the patient;

said top end including a slot through which used patches may be inserted for collection in said housing, whereby the unit can be used to store and dispense unused patches as well as collected and store used patches therein for subsequent disposal.

* * * * *